United States Patent
Chen (12)

(10) Patent No.: US 6,416,531 B2
(45) Date of Patent: *Jul. 9, 2002

(54) APPLICATION OF LIGHT AT PLURAL TREATMENT SITES WITHIN A TUMOR TO INCREASE THE EFFICACY OF LIGHT THERAPY

(75) Inventor: James C. Chen, Bellevue, WA (US)

(73) Assignee: Light Sciences Corporation, Issaquah, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/103,761

(22) Filed: Jun. 24, 1998

(51) Int. Cl.[7] .............................................. A61B 18/20
(52) U.S. Cl. ............................. 607/89; 606/10; 606/13; 604/20; 128/898
(58) Field of Search .................. 606/2, 3–19; 128/898; 607/88–96, 98–101; 604/20

(56) References Cited

U.S. PATENT DOCUMENTS

| | | | |
|---|---|---|---|
| 4,336,809 A | | 6/1982 | Clark |
| 4,651,739 A | * | 3/1987 | Oseroff et al. ................. 607/88 |
| 5,000,752 A | * | 3/1991 | Hoskin ........................... 606/9 |
| 5,445,608 A | * | 8/1995 | Chen et al. .................... 604/19 |
| 5,514,669 A | | 5/1996 | Selman ......................... 514/63 |
| 5,715,837 A | | 2/1998 | Chen ........................... 128/899 |

OTHER PUBLICATIONS

"Optical Dosimetry for interstitial photodynamic therapy" by Arnfield et al; Med Phys vol. 16 No. 4; Jul.–Aug./1989; pp. 603–608.*

* cited by examiner

Primary Examiner—David M. Shay
(74) Attorney, Agent, or Firm—Ronald M. Anderson

(57) ABSTRACT

Light is administered during photodynamic therapy (PDT) for an extended period of time at a plurality of sites distributed within the abnormal tissue of a tumor. A clinical study has shown that a substantially greater volume of abnormal tissue in a tumor is destroyed by the extended administration of light therapy from a plurality of probes than would have been expected based upon the teaching of the prior art. In this process, a plurality of light emitting optical fibers or probes are deployed in a spaced-apart array. After a photoreactive agent is absorbed by the abnormal tissue, the light therapy is administered for at least three hours. The greater volume of necrosis in the tumor is achieved due to one or more concomitant effects, including: the inflammation of damaged abnormal tissue and resultant immunological response of the patient's body; the diffusion and circulation of activated photoreactive agent outside the expected fluence zone, which is believed to destroy the abnormal tissue; a retrograde thrombosis or vascular occlusion outside of the expected fluence zone; and, the collapse of the vascular system that provides oxygenated blood to portions of the tumor outside the expected fluence zone. In addition, is possible that molecular oxygen diffusing and circulating into the expected fluence zone is converted to singlet oxygen during the extended light therapy, causing a gradient of hypoxia and anoxia that destroys the abnormal tissue outside the expected fluence zone.

26 Claims, 7 Drawing Sheets

APPLICATION OF LIGHT AT PLURAL TREATMENT SITES WITHIN A TUMOR TO INCREASE THE EFFICACY OF LIGHT THERAPY

FIELD OF THE INVENTION

The present invention generally relates to the use of light therapy to destroy abnormal tissue in a tumor, and more specifically, to the use of multiple light sources disposed at spaced-apart treatment sites within a tumor to render the therapy.

BACKGROUND OF THE INVENTION

Abnormal tissue in the body is known to selectively absorb certain dyes that have been perfused into a treatment site to a much greater extent than surrounding tissue. For example, tumors of the pancreas and colon may absorb two to three times the volume of these dyes, compared to normal tissue. Once pre-sensitized by dye tagging in this manner, the cancerous or abnormal tissue can be destroyed by irradiation with light of an appropriate wavelength or waveband corresponding to an absorbing wavelength or waveband of the dye, with minimal damage to normal tissue. This procedure, which is known as photodynamic therapy (PDT), has been clinically used to treat metastatic breast cancer, bladder cancer, lung carcinomas, esophageal cancer, basal cell carcinoma, malignant melanoma, ocular tumors, head and neck cancers, and other types of malignant tumors. Because PDT may selectively destroy abnormal tissue that has absorbed more of the dye than normal tissue, it can successfully be used to kill the malignant tissue of a tumor with less effect on surrounding benign tissue than alternative treatment procedures.

The effectiveness of PDT for treating tumors has become increasingly more evident to the medical community. Each year, numerous papers are published disclosing research that has been carried out to explore how PDT can more effectively be used and to better understand the processes by which PDT destroys abnormal cells. Much of the prior art discloses the use of relatively high powered lasers as an external light source employed to administer the light to a treatment site. Typically, the light from an external laser source is conveyed through an optical fiber to a treatment site on the skin of a patient or to an internal site within the patient's body. Penetration of a tumor by the optical fiber is achieved either through a small incision in the overlying dermal layer, or directly, if the tumor is surgically exposed.

Most applications of PDT are conducted using a single optical fiber to provide the light therapy. An optical fiber used to render PDT may include a diffuser on its distal end to enhance the radial distribution of light from the fiber. Light emitted through the diffuser more fully illuminates a treatment site within a tumor in which the optical fiber has been inserted.

Research has been conducted to measure the penetration depth of light into tissue as a basis for assessing the volume of tissue that will be affected by the light applied to a treatment site to render PDT. This research has determined that the penetration depth (or a reciprocal value corresponding to the light attenuation of the tissue) depends upon the wavelength of the light, the type of tissue, the direction of irradiation, the oxygenation of the tissue, the striation of the tissue, the perfusion of blood in the tissue at the site, and other physiological and physical factors. Generally, at a wavelength of about 630 nm, the depth of penetration of light into tissue has been found to be between about 0.2 mm and 7 mm, depending upon the type of tissue (as reported in "In Vivo Measurement of the Optical Interaction Coefficients of Human Tumors at 630 nm," I. Driver, C. P. Lowdell, and D. V. Ash, Phys. Med. Biol., Vol. 36, No. 6, pp. 805–813, Table 3, (1991). Further, this paper reported a large inter-sample variation for the depth of light penetration in the same type of tissue. Tissue of a darker color, such as that of the liver, greatly attenuates light transmission, while brain tissue tends to scatter the light and thus limits light penetration. Generally, longer wavelength light penetrates more deeply, but most of the currently available photoreactive reagent dyes used for PDT have absorption wavebands in the 600–700 nm range.

The limited penetration depth of light in tissue would seem to indicate that light emitted at a single treatment site to render PDT will be effective in destroying abnormal tissue in only a relatively small volume within a tumor. To treat larger tumors, multiple light treatment sites would be expected to linearly expand the volume as a function of the number of light treatment sites used, i.e., the total volume of the effective zone in a tumor treated with the multiple optical fibers should be equal to the product of the volume treated at one site and the number of sites. In a paper entitled "Photodosimetry of Interstitial Light Delivery to Solid Tumors," M. C. Fenning, D. Q. Brown, and J. D. Chapman, Medical Physics, Vol. 21, No. 7, pp. 1149–1156 (July 1994), reported on research in which both anaplastic and well-differentiated Dunning prostate adenocarcinomas were illuminated in anesthetized Fisher X Copenhagen rats by light from single-fiber and multiple-fiber. illuminators. Each illuminator consisted of a 2 cm laterally diffusing optical fiber placed within a plastic brachytherapy needle implanted into a tumor. The radial falloff of intensity with distance from single fibers was used to determine light attenuation coefficients for various wavelengths, by employing a two-dimensional (2D) photodosimetry computer code. The coefficients were used to calculate relative light intensities in planes perpendicular to the single-fiber and various multiple-fiber configurations. Relative light intensities measured along tumor tracks were compared with those predicted by the 2D photodosimetry evaluation and were found to agree within ±14%, for all configurations of the optical fibers studied. It was noted that at wavelengths equal to and greater than about 700 nm, optical fiber spacings of at least one cm produced relatively uniform light fields (±20%) in tumor planes perpendicular to the optical fibers. At line 32 of the second column on page 1155 of the paper, it is noted that:

> For human tumors with light attenuating properties similar to the R3327-H tumor, the heterogeneity of light dose in tumor volumes delivered by a multifiber illuminator with 1.0-cm spacings will be considerably greater than ±20%. Illumination of tumors by such procedures will produce relatively large variations in biological effect by interstitial PDT. Furthermore, to expose all tumor tissue to a minimum light dose required for a specific biological effect, large fractions of the tumor would of necessity be overdosed. While this may not seriously impact upon tumor response, it will limit the volume of solid tumor which can be treated with a specific time by a specific light source. Laser output intensity has not been a limiting factor for the illumination of superficial lesions in clinical studies to date. Nevertheless, to successfully scale up this procedure for the treatment of bulky human tumors, laser output intensity and tumor volume will determine the time required to deliver a curative light dose.

The paper further concludes that more than seven optical fibers may be required to properly treat a tumor with PDT, to guarantee that adequate light is delivered, particularly to the periphery of a tumor, due to the rapid falloff of light at the edge of the illuminated field. The reference thus teaches or suggests that the effect of PDT on a human tumor, particularly one of larger size, will be limited to the region of the tumor directly viably illuminated by the plurality of optical fibers and implies that it will be necessary to repeat the treatment to different areas of the tumor by moving the plurality of the optical fibers so that direct illumination of a greater treatment volume can be accomplished.

The effects of PDT and the manner in which it destroys tissue are not clearly understood. It is believed that the primary mechanism by which PDT destroys cells relies upon the conversion of molecular oxygen to singlet oxygen and the release of free radicals by the light activated dye. In "How Does Photodynamic Therapy Work?" by B. W. Henderson, and T. J. Dougherty, Photochemistry and Photobiology, Vol. 55, No. 1, pp. 145–157 (1992), it is noted that following the absorption of light, a sensitizer is transformed from its ground state to an excited triplet via a short-lived singlet state. The excited triplet can react directly either with a substrate or solvent by hydrogen atom or electron transfer to form radicals and radical ions (Type I reaction) or it can transfer its energy to oxygen directly to form singlet oxygen, which is a highly reactive species (Type II reaction). The paper states that indirect evidence suggests singlet oxygen is the major damaging species in PDT. Based on this belief, the reference concludes that PDT effects should be oxygen-dependent, with full effects of PDT being observed in vitro at oxygen concentrations of about 5%. It is reported by the reference that "no photosensitization can be observed in the absence of measurable oxygen." Further, the reference teaches that the diffusion distance of singlet oxygen in cells is about 0.1 $\mu$m, so that cell damage caused by singlet oxygen will occur close to its locus of generation. Singlet oxygen causes a loss of cell integrity by a photoperoxidation of membrane cholesterol and other unsaturated phospholipids. Associated with the cell membrane damage is a release of inflammatory and immune mediators. Also released through mast cell degranulation is histamine. The substances released are vasoactive, either constrictive or dilatory, and it is believed that they induce vascular damage. Tumor necrosis factor (TNF) is also released, and it too can cause vascular damage. The degree of vascular photosensitivity in tissue appears to be a function of the level of the circulating photoreactive agent. This reference reports that vascular damage in a tumor microenvironment induces hypoxic tumor cell fractions. A key conclusion stated in the paper is that the "rapid shift of cells into hypoxia [after PDT], where they are protected from further PDT damage due to the oxygen limitation of the photodynamic processes, is potentially limiting to direct tumor cell photodestruction." In essence, this statement indicates that efficacy of PDT in destroying tumor cells quickly diminishes after the light activation due to the self limiting effects of hypoxia caused by photovascular occlusion. In other words, the paper concludes that the resulting vascular occlusion limits further blood flow to the treatment site, which is necessary to supply additional molecular oxygen to the tumor cells for use in generating more singlet oxygen.

Also reported in the last cited reference is an observed infiltration of PDT-treated tissue with lymphocytes, plasma cells and histiocytes, which suggests an immune response to effects of the PDT. In high dose bladder PDT treatments, high levels of interleukin 1-beta, interleukin 2, and TNF-alpha have been observed in patients' urine for up to 50 days following the therapy, concurrent with severe inflammatory symptoms. The relative extent of abnormal cell necrosis caused by generation of singlet oxygen and free radicals compared to that resulting from the immune response is not clear from the prior art.

It has been shown that illuminating abnormal cells, which have absorbed a photoreactive agent, with relatively low levels of light for extended periods of time may be even more effective in rendering PDT than the more conventional approach of using a high intensity laser light source to administer light for short time intervals. In commonly assigned U.S. Pat. No. 5,445,608, a plurality of transcutaneously implantable probes that include relatively low intensity light sources are disclosed for rendering PDT to treatment sites within a patient's body. Such probes can be implanted interstitially within a tumor to administer PDT for many hours or days. As necessary, repetitive infusions of a suitable photoreactive agent can be made to sensitize the abnormal cells comprising the tumor so that they are susceptible to being destroyed by the PDT. An apparent question arises in regard to the efficacy of such an approach to treating a relatively large tumor. In view of the teaching of the art discussed above, one would be led to conclude that low intensity light sources on an interstitial probe would lack adequate penetration into a large tumor mass to treat more than a relatively small portion of the tumor—even if plural probes of this type were used. In addition, the prior art suggests that extended PDT delivered to a treatment site will not be effective in a large tumor due to the hypoxia resulting from vascular damage and the vasculature constriction that occurs soon after the PDT commences.

Application of PDT to a larger tumor would seem to require that a plurality of optical fibers spaced sufficiently close together and of sufficient number be inserted into the tumor to ensure that the light intensity between the optical fibers is substantially uniform throughout the volume of the tumor being treated. However, in view of the teaching of the prior art, implanting sufficient numbers of optical fibers or low light intensity probes to provide such uniform illumination does not seem to be a practical approach for treating a larger tumor. The expected effective zone of PDT would seem to be too limited due to the relatively shallow penetration of light into the tissue to justify the use of PDT to treat a large tumor.

SUMMARY OF THE INVENTION

Contrary to the suggestion of the prior art, it appears that PDT can be successfully used for treating larger tumor masses, and that the depth of light penetration into tumor tissue when effecting PDT is not so limiting as indicated in the prior art, in determining the true extent of the effectiveness of the therapy. Indeed, the effective zone of PDT in large tumors has been found to be much larger than the volume of the tumor into which light administered has previously been found to penetrate. Furthermore, the effectiveness of the PDT in treating a larger volume of a tumor appears to be more dependent upon a pattern in which light emitting sites are arrayed in the tumor than previously known.

In accord with the present invention, a method is defined for destroying abnormal tissue in a tumor within a patient's body using an extended light therapy and at least one concomitant effect thereof. The method includes the step of administering a photoreactive agent to the abnormal tissue. The photoreactive agent, which has a characteristic absorption waveband, is preferably absorbed by the abnormal tissue rather than by normal tissue in the patient's body. Light having a waveband corresponding to the absorption waveband of the photoreactive agent is administered to a treatment zone in the tumor. A pattern in which the light is administered to the tumor defines the treatment zone, and this zone preferably encompasses a substantial portion of the tumor not penetrated by the light being administered. The method provides for continuing to administer the light to the treatment zone for at least three hours of extended light therapy. The light destroys the abnormal tissue that it illuminates by activating the photoreactive agent absorbed thereby. Furthermore, the extended period of light therapy indirectly destroys the substantial portion of the tumor that is not penetrated by the light being administered by inducing at least one concomitant effect that destroys the abnormal tissue comprising the substantial portion of the tumor.

In one case, the concomitant effect arises because the destruction of the abnormal tissue in the treatment zone deprives the substantial portion of the tumor from receiving oxygen. The abnormal tissue in the substantial portion of the tumor is thus destroyed due to oxygen depletion.

In another instance, the concomitant effect arises because the photoreactive agent within the treatment zone that is activated by the light being administered diffuses into the substantial portion of the tumor that is not penetrated by the light. This photoreactive agent that is thus activated then destroys the abnormal tissue in the substantial portion of the tumor not directly penetrated by the light.

In yet another instance, the concomitant effect arises because the light therapy causes necrosis of the abnormal tissue in the treatment zone, which causes either an immune response or an inflammation in the patient's body that destroys the abnormal tissue in the substantial portion of the tumor not directly penetrated by the light.

In still another instance, the concomitant effect arises because the destruction of abnormal tissue in the treatment zone causes either a vascular collapse, stasis, or occlusion, so that blood flow to the substantial portion of the tumor that is not directly penetrated by the light is terminated, causing the abnormal tissue in that substantial portion to die.

In one embodiment of the method, the light is administered through an optical fiber from a source that is external to the patient's body. The method further preferably includes the step of implanting a plurality of probes for administering the light into the tumor at spaced-apart locations within the treatment zone. In one embodiment, the light is then administered from at least one light source included on each of the plurality of probes. In another embodiment, the light is delivered to the plurality of probes through a plurality of optical fibers from a source that is external to the patient's body. The treatment zone is not more than about 3 cm from each of the plurality of probes.

In the method, the light administered to the treatment zone produces singlet oxygen, which depletes oxygen from the substantial portion of the tumor that is outside the treatment zone, causing a gradient of hypoxia and anoxia in that portion of the tumor, which leads to a destruction of the abnormal tissue contained therein.

The method may include further steps. Specifically, in one embodiment, the light is emitted into the tumor in a first direction from each of the plurality of probes, relative to the probe from which the light is emitted. Next, the method provides for terminating emission of light into the tumor in the first direction and emitting light into the tumor in a second direction from each of the plurality of probes. The second direction is substantially different from the first direction for each of the probes. Preferably, in one embodiment, the first direction is directed toward a perimeter of the tumor, and the second direction is directed toward an interior of the tumor. By first destroying the perimeter of the tumor, the interior portion of the tumor is more readily destroyed due to the one or more concomitant effects.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
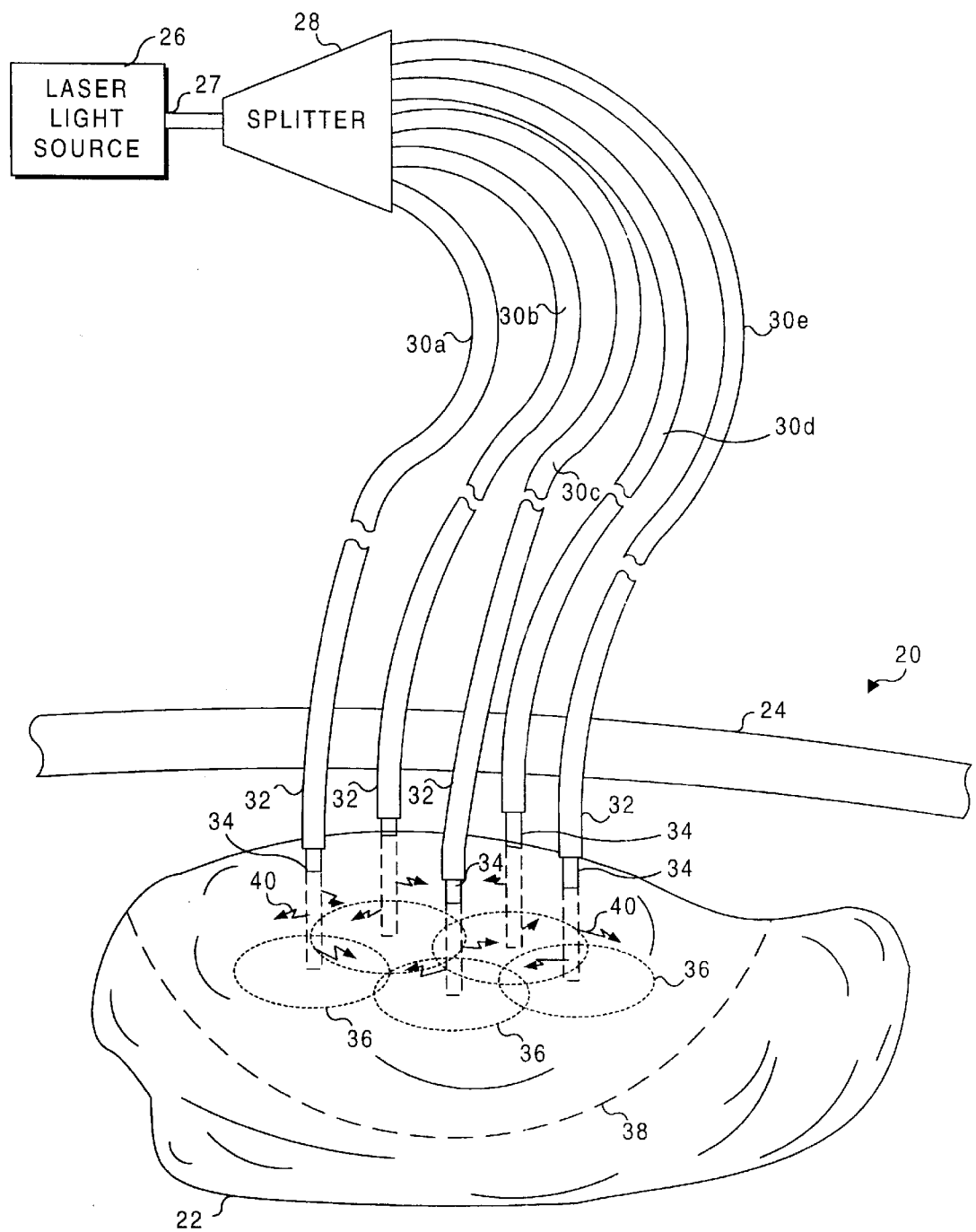
FIG. 1 is a schematic drawing illustrating a side elevational view of a first embodiment of the present invention for administering light to a treatment site within a tumor in a patient's body.

With reference to FIG. 1, the present invention is illustrated in connection with treating a tumor 22 that is disposed within a patient's body 20. Tumor 22 is relatively large, having a length of approximately 7 to 10 cm and a transverse width of about 7 cm in this exemplary illustration. The tumor is disposed below a dermal layer 24, for example, within the patient's abdominal cavity.

In the present invention, PDT plays an important role is destroying abnormal tissue comprising tumor 22. As is done when rendering conventional PDT, a photoreactive agent is administered to the patient either orally or by injection and is selectively preferentially absorbed by the abnormal tissue of tumor 22. Thereafter, using a surgical procedure to access tumor 22 through dermal layer 24, or using an endoscopic procedure with minimally invasive impact, a plurality of optical fibers 30a–30e are inserted into the interior of tumor 22 in a spaced-apart array so that the optical fibers are arranged in a pattern that is more likely to increase the effectiveness of the therapy administered to the tumor. A laser light source 26 produces light lying within the light absorption waveband of the photoreactive agent that has been administered to the patient.

Light emitted by laser light source 26 is conveyed through an optical fiber 27 to a splitter 28 that divides the coherent light so that it is equally distributed among optical fibers 30a–30e. The light is conveyed through these optical fibers toward their distal ends. Optical fibers 30a–30e include an outer cladding 32 that minimizes losses through the outer surface of the optical fiber, insuring that substantially all of the light input to the optical fibers at their proximal ends, i.e., at splitter 28, is conveyed through the optical fibers to their distal ends, which have been inserted interstitially into the interior of tumor 22.

In the embodiment illustrated in FIG. 1, cladding 32 is removed from approximately the last 3 to 4 cm of the distal ends of each of optical fibers 30a–30e, exposing a core 34. A diffusing surface is provided on the exposed portion of core 34, e.g., by roughening the surface of the exposed core, thereby insuring that light conveyed through the optical fibers is uniformly distributed through the sides and through the distal ends of the optical fibers inserted into the tumor. Light emitted by the exposed distal ends of each of these optical fibers penetrates tumor 22 to an effective depth of less than 1.5 cm. The penetration depth of the emitted light into the tumor determines a generally cylindrical expected fluence zone 36, the radius of which is indicated by the dotted circles shown in FIG. 1, and more clearly, in the plan view of FIG. 2.

Figure 2:
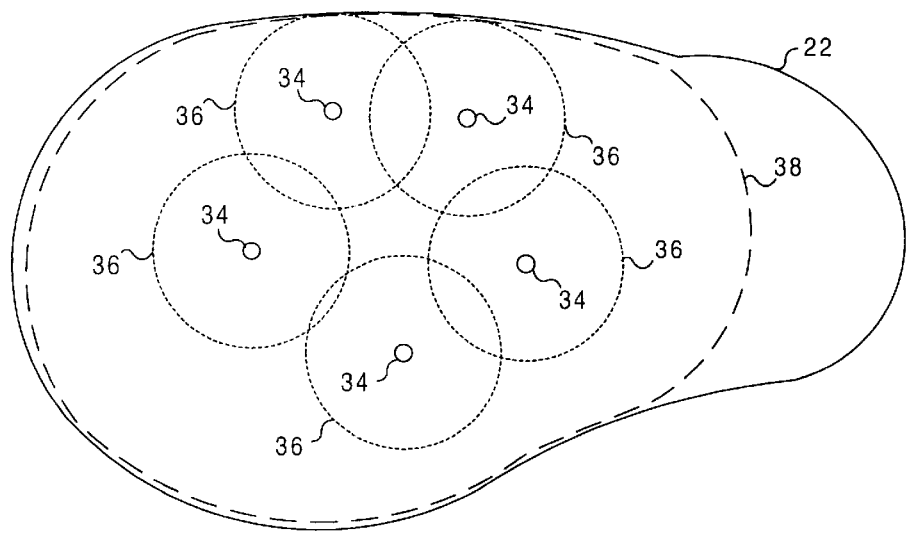
FIG. 2 is a plan view of the tumor shown in FIG. 1, illustrating the positions of probes and the radial depth to which light emitted thereby directly penetrates into the tumor.

As will be evident from FIG. 2, the exposed portions of cores 34 from which the cladding has been removed are inserted into tumor 22, generally forming a circle in which the expected fluence zones 36 around each optical fiber at least partially overlap. It should also be noted that the expected fluence zone for each optical fiber is determined partly by the intensity of the light delivered to the distal ends of each of the optical fibers and partly by the nature of the abnormal tissue in tumor 22. Measurements in the prior art indicate that for most tumor tissue, the maximum effective depth of light penetration (at a wavelength of 600–700 nm) within tumor tissue is less than 1.5 cm. Furthermore, the effective depth of the expected fluence zones is substantially less than the maximum, depending upon a number of factors such as the blood concentration in the tissue, color of the tissue, the photoreactive agent concentration, etc.

In conventional PDT, light at relatively high intensity is delivered to a treatment site within a tumor through one or more optical fibers for a relatively short period of time, typically much less than one hour. In the prior art, the effect of the PDT is believed to be limited to the expected fluence zones, i.e., to the volume of the tumor directly illuminated by the light emitted from the optical fiber(s). In contrast, in the exemplary arrangement of optical fibers shown in FIGS. 1 and 2, a relatively lower intensity light is provided from laser light source 26 at the distal end of each of optical fibers 30a–30e, and the light therapy extends for a period of time greater than three hours—up to several days in duration. During this extended period of light therapy, additional photoreactive agent may be administered to the patient, depending upon the size of the tumor, the type of photoreactive agent used, and other conditions unique to each patient.

By administering lower intensity light for an extended period of time in this manner, the light therapy has been found to destroy a much larger volume than expected. Based on the teaching of the prior art, only abnormal tissue that has absorbed the photoreactive agent and has been directly illuminated by light emitted by each of the optical fibers within their expected fluence zones should be destroyed by the PDT. As a result of the extended period of treatment using the plurality of optical fibers shown in FIGS. 1 and 2, a substantially expanded necrotic zone 38 in tumor 22 should be achieved in which the abnormal tissue well outside the expected fluence zones of each of the optical fibers is destroyed. The substantially greater volume of necrotic zone 38 in tumor 22 is believed to be due to one or more causes that are concomitant to the destruction of abnormal tissue by conventional PDT achieved during a conventional short-term light therapy.

It is believed that the abnormal tissue outside the expected fluence zones around each optical fiber is destroyed due to one or more other factors or processes that differ from the process involved in conventional short-term PDT. The extended duration PDT of the present invention is believed to cause an inflammation of the damaged abnormal tissue in the expected fluence zone, which then gives rise to the augmentation of a natural immune response of the patient's body. The natural immune response then destroys the abnormal tissue outside expected fluence zones 36. While an immune response by the patient's body prior to the onset of the extended period of light therapy is not triggered by the presence of abnormal tissue in tumor 22, it is believed that the extended period of light therapy administered under the present invention may trigger inflammation and the immune response of the patient so that the abnormal tissue outside the expected fluence zones is attacked and destroyed by the patient's own system.

Another possible cause for the expanded volume in which necrosis of the abnormal tissue in tumor 22 will occur in connection with the present invention is the oxygen depletion outside the expected fluence zones that arises due to the generation of singlet oxygen as light is administered to tumor 22 through the optical fibers. Since the light is administered for an extended period of time, the conversion of molecular oxygen into singlet oxygen continues to occur during the duration of the treatment, contrary to the teaching of the prior art, as more molecular oxygen diffuses into the expected fluence zones. The conversion of molecular oxygen that proceeds during the extended administration of light therapy depletes the oxygen available to the abnormal tissue outside the expected fluence zones, causing a gradient of hypoxia and anoxia in the portion of the tumor that is not directly illuminated by light. This continuing photodynamic transformation of molecular oxygen to singlet oxygen by the excited photoreactive agent within the expected fluence zones thus has an effect that expands outside those zones. In addition, it is possible that singlet oxygen produced in the expected fluence zones diffuses or circulates into the larger volume of the tumor outside these zones.

Another possible cause of the expanded necrotic zone achieved by the present invention is the spread of activated photoreactive agent from within the expected fluence zones into other portions of the tumor outside these zones. Once activated by light administered during the extended period of light therapy, the photoreactive agent diffuses and circulates outside the expected fluence zones and into other portions of the tumor, where it may destroy abnormal tissue. It is believed that the photoreactive agent that has been activated during the extended period of light therapy may itself have a destructive effect on abnormal tissue that subsequently absorbs it, and that this destructive effect is not oxygen dependent. The prior art has taught that the conversion of molecular oxygen to singlet oxygen is the primary cause of the destruction of abnormal tissue arising from conventional PDT, and that this conversion occurs only during a brief interval at the onset of the light therapy administration. However, the present invention achieves a substantially greater destruction of abnormal tissue over a substantially longer period of time than should be possible if this teaching of the prior art were correct. Thus, the present invention achieves an unexpected result that the prior art has taught should not be possible.

A further possible cause of the expanded necrotic zone obtained with the present invention is a vascular stasis, collapse, or occlusion occurring outside the expected fluence zones, due to any of the other concomitant factors discussed above, or due to any venous injury and thrombosis occurring within the expected fluence zones that propagate outside those zones. The vascular stasis, collapse, and occlusion occurring as a result of venous injury is known in the medical art, but has not previously been observed or disclosed as giving rise to an expanded volume of necrosis in a tumor following an extended period of light therapy.

There is another possible explanation for the much larger volume of abnormal tissue destroyed in accord with the present invention. Light applied to the abnormal tissue in the tumor is likely to be scattered along random paths within the tissue that may penetrate to a substantially greater depth within tissue, although at very much attenuated intensity. Accordingly, it may be that the expected fluence zone, which represents the limit of direct penetration of light, does not accurately define the full extent of the penetration of the scattered and reflected light within the abnormal tissue. This scattered and reflected light may be of too low an intensity to have much effect when administered for the relatively short duration of a conventional PDT procedure, but may have a much more pronounced effect when delivered for the extended duration of the present invention, so that the conversion of molecular oxygen to singlet oxygen occurs at a much greater depth within the tumor than the expected fluence zone would indicate.

The present invention is clearly not limited to administering light for an extended period of time using a laser source. Instead, almost any source of light can be used that emits light in the appropriate waveband, i.e., corresponding to the absorption waveband of the photoreactive agent. For example, the light source may comprise an electroluminescent device, an LED, a fluorescent light source, an incandescent light source, an arc lamp, or other source of light that is conveyed to a tumor through an optical fiber (or light pipe), or is disposed on a probe that is inserted into the tumor. Since the light is administered to the tumor for an extended period of time, it is generally preferable to implant the source of the light directly into the tumor at a plurality of sites and to energize the light sources with an electrical current from a power supply that is internal to the patient's body. It is undesirable for optical fibers or power leads to extend through the dermal layer of a patient's body for an extended period of time, since such practices are known to create a potential increased risk of infection. Instead, probes or light bars having a plurality of LEDs or other light sources disposed therein are preferably implanted within the tumor and energized using an implanted power source. An implanted conductive coil can be energized by electromagnetically coupling power across the dermal layer from an external coil connected to an alternating current source, or by otherwise producing a varying electromagnetic field outside the patient's body that is coupled to the implanted coil. U.S. Pat. No. 5,715,837, which is assigned to the same assignee as the present invention, discloses details of apparatus useful for this purpose, and its disclosure and drawings are hereby specifically incorporated herein by reference.

Figure 3:
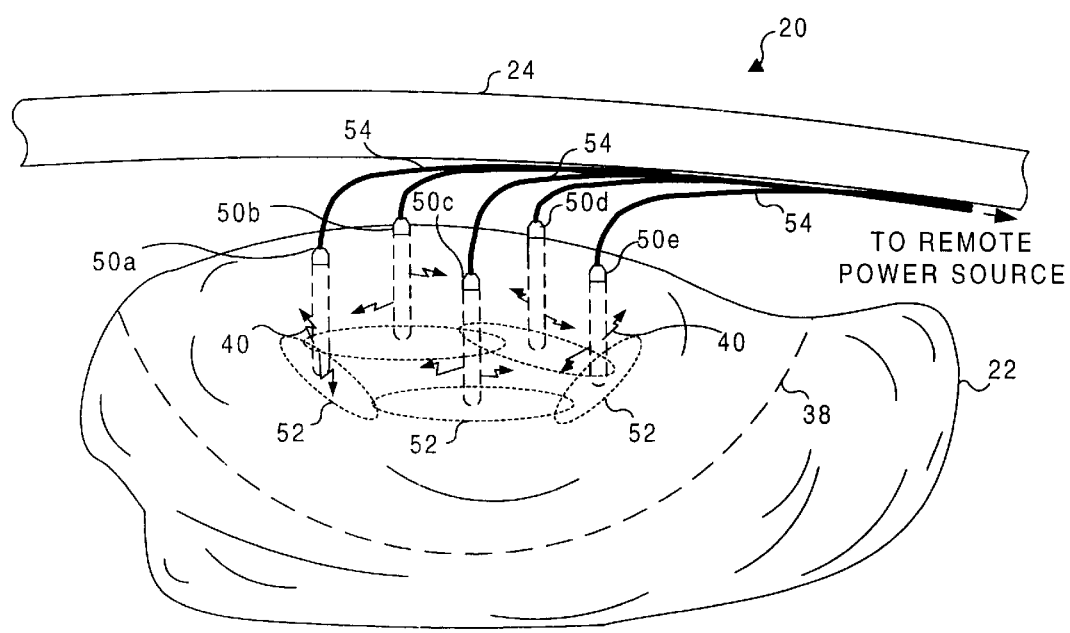
FIG. 3 is a side elevational view of a second embodiment of the present invention, showing the tumor with a plurality of light emitting implanted probes inserted therein.
Figure 4:
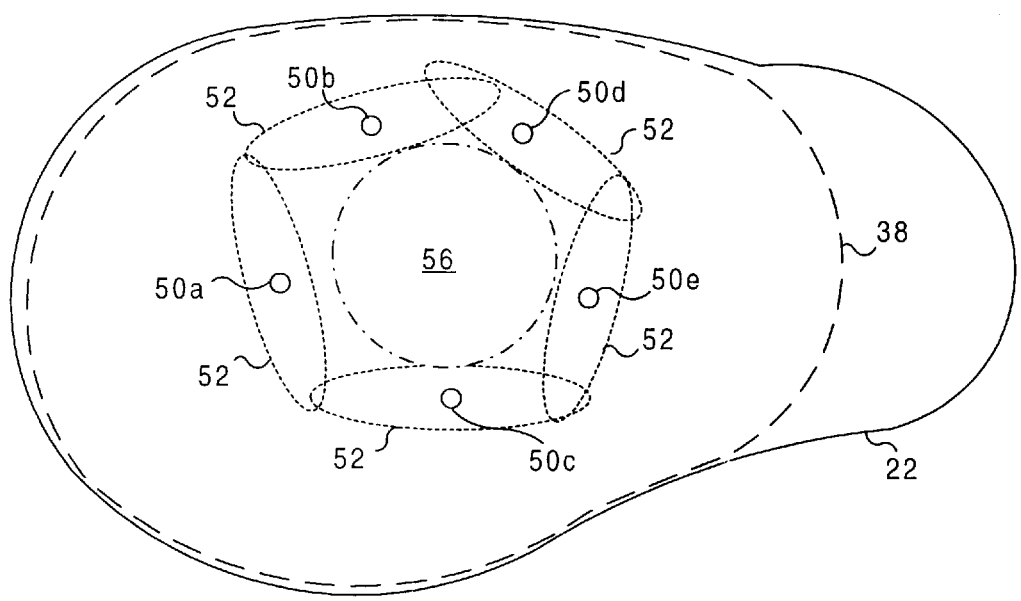
FIG. 4 is a plan view of the tumor shown in FIG. 3, illustrating the direct light penetration pattern for each of the probes.

FIG. 3 illustrates implanted probes 50a–50e, which have been inserted into tumor 22 in a generally circular pattern. As shown more clearly in FIG. 4, each of probes 50a–50e has a generally elliptical expected fluence zone 52, since the light is emitted from opposite sides of each probe and is not uniformly constant in a radial direction around the longitudinal axis of the probes. As shown in FIG. 4, the expected fluence zones of probes 50a–50e generally overlap, forming a rough circle that encompasses or surround a central zone 56, which does not receive any direct light emitted by the probes. Although conventional short-term PDT would destroy the abnormal tissue within expected. fluence zones 52, the present invention provides for administering the light therapy for a much longer or extended period of time that enables abnormal tissue in a substantially larger volume comprising necrotic zone 38 of tumor 22 to be destroyed. Necrotic zone 38 includes central zone 56, which is surrounded by expected fluence zones 52. Each of probes 50a–50e is coupled to the remote power source (not shown) through leads 54. The remote power source can comprise a battery or storage capacitor which store sufficient energy to provide the relatively low intensity light emitted by each of light probes 50a–50e, and/or may comprise an implanted coil that receives electromagnetic energy from an external source (neither shown), as noted above.

Another aspect of the present invention arises from positioning the probes in a pattern such as that shown in FIGS. 3 and 4. This aspect of the present invention relates to the effect on central zone 56 of the necrosis of abnormal tissue occurring in expected fluence zones 52 due to PDT. Since these expected fluence zones substantially surround central zone 56, all of the blood vessels that supply oxygenated blood to the central zone pass through these zones. The destruction in the expected fluence zones of blood vessels supplying oxygenated blood to central zone 56 should cause abnormal tissue within central zone 56 to be destroyed due to oxygen and nutrient starvation. However, since the present invention will produce necrotic zone 38 that extends radially outward of the expected fluence zones, the present invention is not limited to a pattern of light probes (or optical fibers) that produce expected fluence zones overlapping to surround a central zone.

Figures 5A, 5B, 5C:
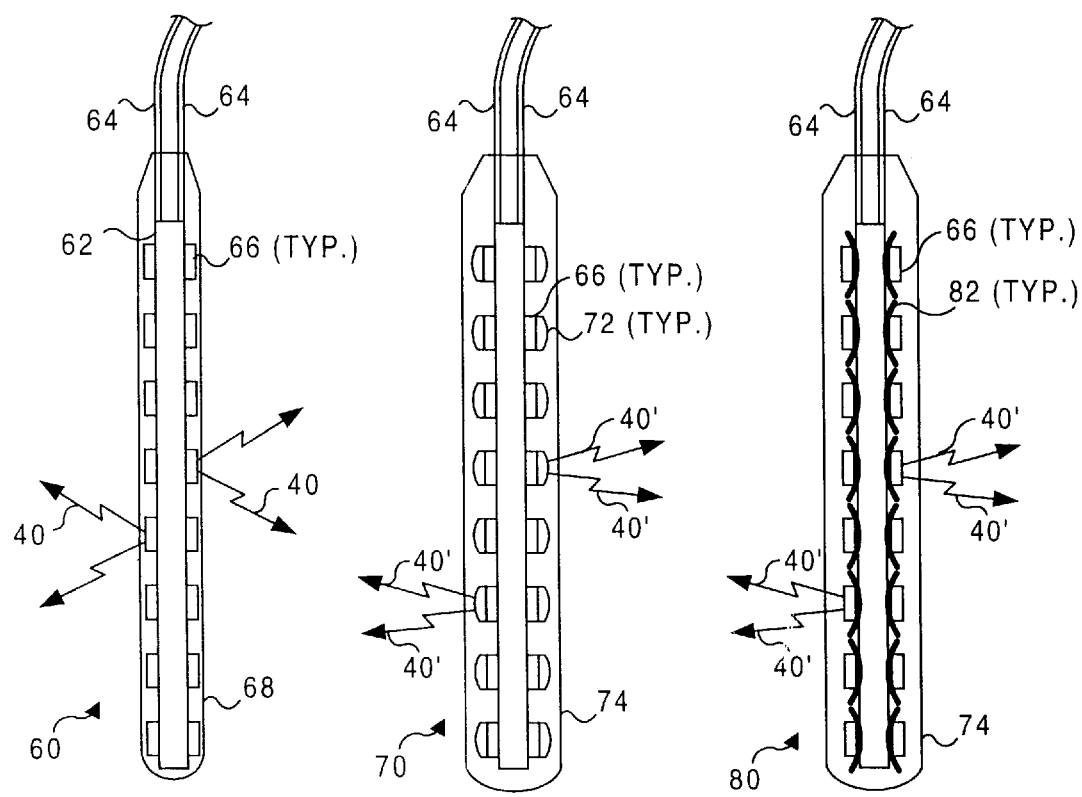
FIGS. 5A–5C are three different embodiments of light emitting probes having a plurality of light sources contained therein.

In FIG. 5A, details of a probe 60 suitable for use in the present invention are illustrated. Probe 60 includes a flexible substrate 62 on which are mounted a plurality of spaced-apart LEDs 66. Leads 64 are coupled to conductive traces (not shown) on flexible substrate 62 and provide electrical current to energize LEDs 66, causing them to emit a light 40 of the appropriate waveband within the light absorption waveband of the photoreactive agent. An optically transparent, biocompatible envelope 68 surrounds LEDs 66 and flexible substrate 62, sealing the structure so that the internal components are not exposed to bodily fluids.

FIGS. 5B and 5C illustrate details of probes 70 and 80, respectively, in which LEDs 66 are also used to emit light. However, in probe 70, lenses 72 are applied over LEDs 66 to focus light rays 40', minimizing the spread of the light emitted by each of the LEDs. In FIG. 5C, concave mirrors 82 are mounted under LEDs 66, also focusing light 40'. Optically transparent, biocompatible envelopes 74 enclose each of probes 70 and 80, providing the same protection against bodily fluids as noted above in connection with envelope 68 of probe 60. By focusing the light emitted by LEDs 66, a more directed pattern defining the elongate shape of expected fluence zones 52 can be achieved with probes 70 and 80.

Figure 6A:
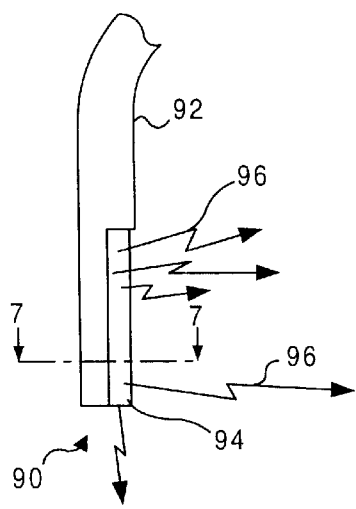
FIGS. 6A and 6B illustrate two different embodiments of an optical fiber probe that emits light in only a preferred direction.
Figure 6B:
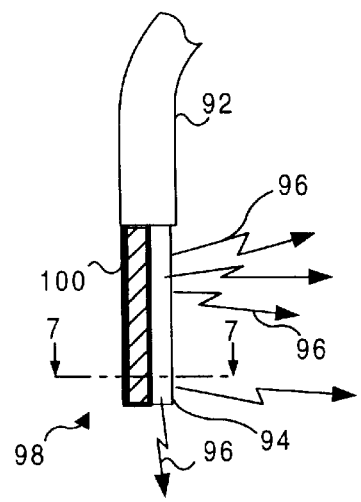
Figure 7:
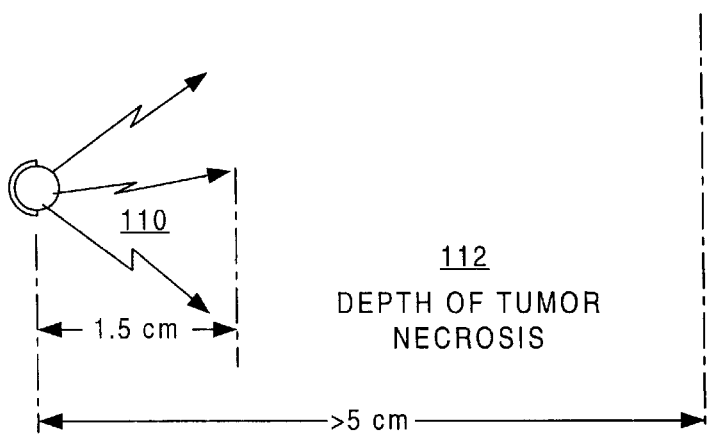
FIG. 7 is a schematic diagram comparing a depth of direct light penetration in a tumor to a depth of tumor necrosis caused by one or more secondary effects.

FIGS. 6A and 6B illustrate optical fibers 90 and 98, in which a distal portion of a core 94 exposed by removing a portion of cladding 92. limits the direction in which light rays 96 are emitted. In optical fiber 90, cladding 92 is removed around approximately one-half the circumference of core 94, adjacent the distal end of the optical fiber, so that light conveyed by the optical fiber is emitted only through the exposed surface of the core and through its end. In optical fiber 98, cladding 92 is removed from the entire portion of the distal end, and a hemispherical mirror coating 100 surrounds approximately one-half of the circumference of the exposed core. Light is thereby reflected from hemispherical mirror surface 100 through the exposed side of core 94. FIG. 7 illustrates a cross-sectional view showing an expected fluence zone 110 extending approximately 1.5 centimeters, and a depth of tumor necrosis 112 that is greater than five centimeters in accord with the present invention. Optical fibers 90 and 98 permit light to be administered in a desired direction during the administration of an extended light therapy. For example, by using either of optical fibers 90 or 98, light can be directed toward the interior of a tumor, and light directed toward the periphery of the tumor can be minimized, thereby avoiding exposure of normal tissue outside the limits of the tumor to the light. The directional emission of light from optical fibers 90 and 98 can also be used to define many different desired patterns for administering light therapy during the extended period in accord with the present invention.

Figure 8:
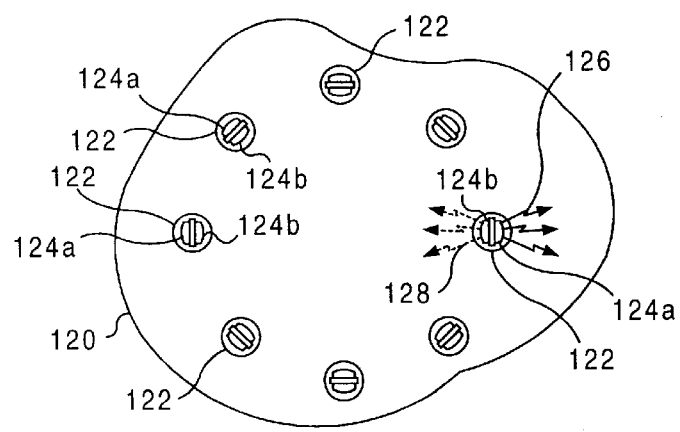
FIG. 8 is a plan view of a tumor showing a plurality of probes that selectively emit light in one of two different directions.

With reference to FIG. 8, a tumor 120 is illustrated in a plan view; a plurality of probes 122 that emit light of an appropriate waveband have been implanted in spaced-apart array within the tumor, generally defining a circle. Each of probes 122 includes two separately energizable groups of light sources that emit light in opposite directions. Specifically, when light sources 124a are energized, light rays 126 are emitted that are generally directed toward the perimeter or periphery of tumor 120. As a further aspect of the present invention, it is contemplated that by initially administering light rays 126 directed towards the periphery of the tumor, destruction of the abnormal tissue comprising tumor 120 will occur first around the periphery of the tumor. Thereafter, light sources 124b are energized, and light sources 124a are de-energized. Light sources 124b emit light rays 128 that are directed toward the inner portion of tumor 120. Necrosis of the abnormal tissue around the periphery of the tumor should tend to cause vascular stasis, collapse, or occlusion of the vascular structure, providing oxygenated blood to the inner portion of tumor 120. Accordingly, the extended light therapy provided by light rays 128 should continue the destruction of abnormal tissue within the interior of tumor 120 and the actual necrotic zone will be extended as a result of one or more of the concomitant factors discussed above. An enhanced necrosis volume within tumor 120 is thus achieved using this two pronged light therapy. As a further benefit, less electrical current is required by each of probes 122, since only a portion of the light sources on each probe are energized at a given time. This reduced electrical current thereby minimizes the capacity of the power source required to energize the probes.

Figure 9:
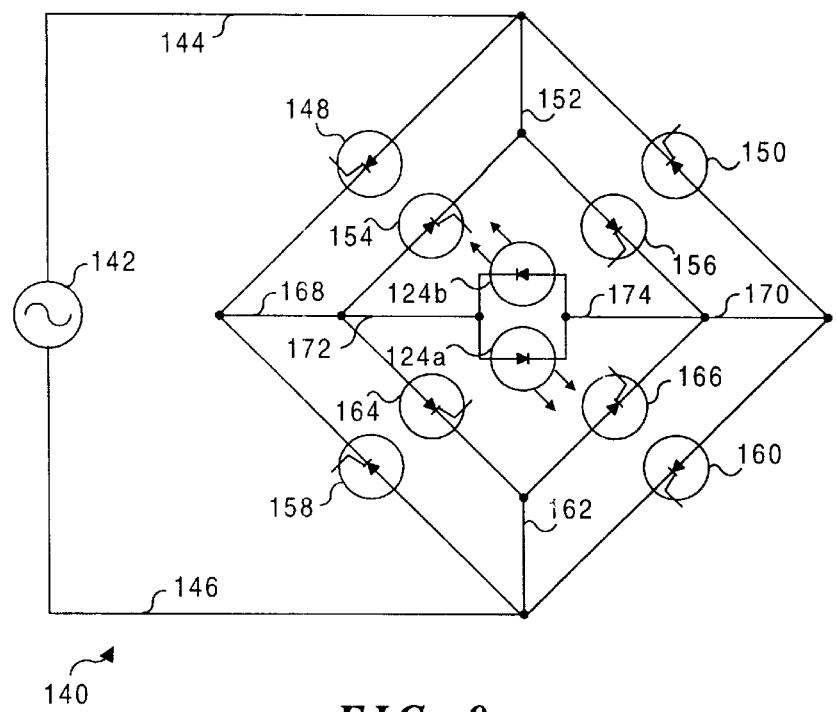
FIG. 9 is an electrical schematic diagram of a circuit that selectively energizes one of two different groups of light emitting diodes (LEDs)

FIG. 9 illustrates a circuit 140 that can be used to selectively energize either light sources 124a or 124b. In this embodiment, the light sources comprise LEDs that only emit light when energized by the proper polarity voltage. Circuit 140 includes a source 142 that supplies an alternating current through conductors 144 and 146. Conductor 144 is coupled to the anode of a silicon controlled rectifier (SCR) 148, to the cathode of an SCR 150, and through a conductor 152 to the cathode of an SCR 154, and the anode of an SCR 156. Similarly, conductor 146 is connected to the anode of an SCR 158, the cathode of an SCR 160, and through a conductor 162, to the cathode of an SCR 164 and the anode of an SCR 166. The cathode of SCR 148, the anode of SCR 154, the cathode of SCR 158, and the anode of SCR 164 are coupled through conductors 168 and 172 to the anode of the LEDs comprising first set of light sources 124a and to the cathode of the LEDs comprising second set of light sources 124b. Similarly, the anode of SCR 150, the cathode of SCR 156, the anode of SCR 160, and the cathode of SCR 166 are coupled through conductors 170 and 174 to the cathode of the LEDs comprising the first set of light sources 124a and the anode of the LEDs comprising the second set of light sources 124b. By selectively gating either SCRs 148, 150, 158, and 160 or SCRs 154, 156, 164, and 166, either first set of light sources 124a or second set of light sources 124b are selectively energized. The gating signal can be transmitted as an RF signal that is received and amplified before application to circuit 140, since the circuit is internally implanted within the patient's body. AC power source 142 can be an internally implanted coil, electromagnetically coupled to an external source of power, as noted above.

Figure 10:
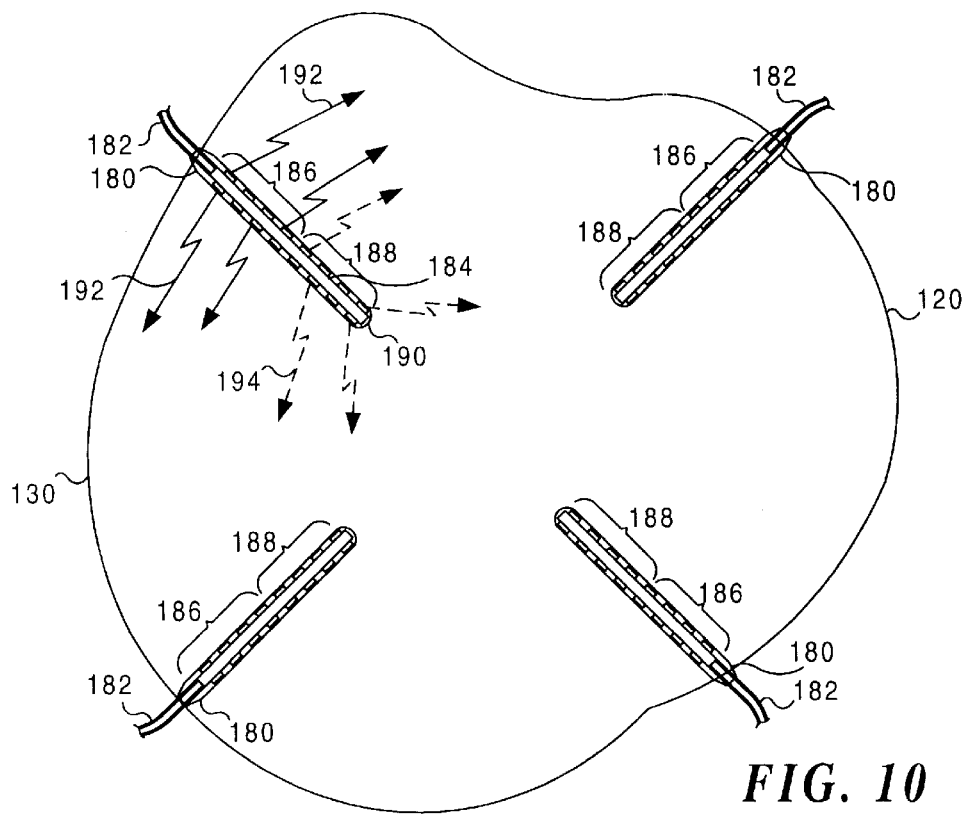
FIG. 10 is a plan view showing an alternative embodiment in which light from two different groups of light sources within each of a plurality of probes is selectively energized.

FIG. 10 illustrates tumor 120 in which probes 180 are inserted generally in a radial direction within the tumor. Probes 180 each include a first set of LEDs 186 that are disposed adjacent an outwardly extending lead 182 of the probe, and a second set of LEDs 188 mounted on a flexible substrate 184 adjacent its inwardly extending distal end. A biocompatible, optically transparent envelope 190 encloses each of probes 180. Initially, first LEDs 186 are energized using circuit 140 so that light rays 192 are emitted from each of probes 180 in the region radially closer to a perimeter 130 of tumor 120. After the photoreactive agent absorbed by tumor 120 has been activated to destroy abnormal tissue adjacent the periphery of the tumor, first set of LEDs 186 are de-energized, and second set of LEDs 188 are energized, emitting light rays 194, which are incident on the inner portion of tumor 120. The concomitant factors occurring as a result of the extended duration of light therapy provided by light rays 192 and 194 thereby destroy substantially all of tumor 120, even though the total volume of tumor 120 is substantially greater than the expected fluence zone for the light sources on probes 180.

Figure 11:
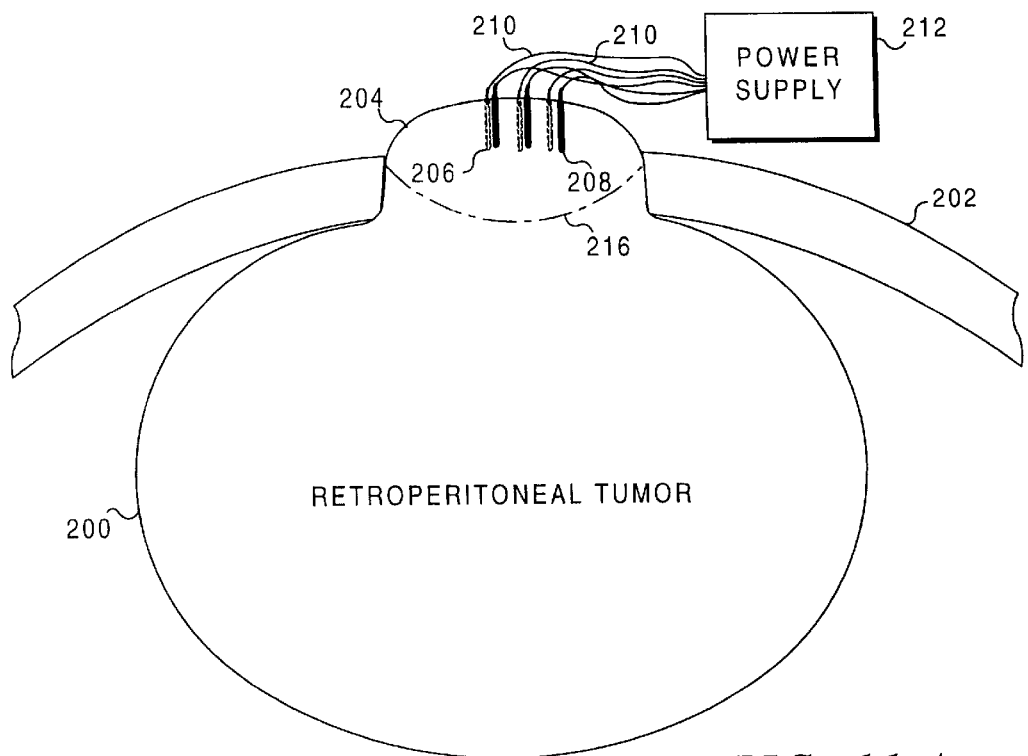
FIG. 11A is a schematic side elevational view of a retroperitoneal tumor within a patient's body that was treated in accord with the present invention.
FIG. 11B is a plan view of the tumor of FIG. 11A showing the disposition of a plurality of probes used to administer PDT to the tumor, the expected fluence zone, and the substantially greater expanded necrotic zone actually achieved.
Figure 11B:
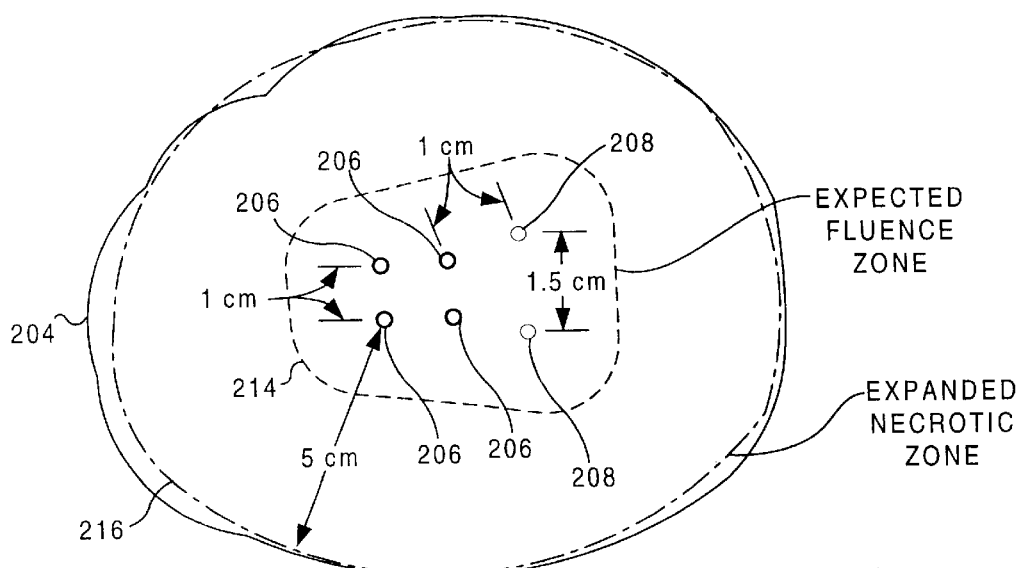

The discovery of the present invention arose in connection with an actual in vivo clinical test on a patient to treat a retroperitoneal tumor 200, generally shaped as shown in FIGS. 11A and 11B. Tumor 200 had been treated previously with chemotherapy and with radiation therapy. Also, attempts had been made to surgically remove it, but tumor 200 had been resistant to each of these conventional forms of treatment. In fact, at the time the clinical study was undertaken, tumor 200 had grown through a dermal layer 202 so that a protruding portion 204 was exposed. In this clinical study, four light bars or probes 206 and two probes 208 were initially inserted into protruding portion 204 of the tumor. Since this portion of the tumor was fully exposed, it was not necessary to surgically or endoscopically implant probes 206 and 208, and the probes could be energized using electrical current from an external power supply 212 supplied through leads 210. The power supplied to produce light at each probe ranged between 25 and 35 mW. The probes were inserted into protruding portion 204 in the pattern illustrated in FIG. 11B. The photoreactive agent aminolevulinic acid (ALA) was administered to the patient approximately five hours prior to energizing probes 206 and 208. Probes 208 were inadvertently pulled from the tumor and were de-activated after approximately 18 hours, leaving the remaining four probes 206 in place and activated for a total of 48 hours.

Four weeks following the administration of the extended light therapy to tumor 200, necrosis in the protruding portion was observed up to approximately five centimeters away from the point where the nearest probe had been disposed. The maximum depth of the necrosis within protruding portion 204 was 5 cm beyond the distal tip of any of the probes. Thus, the extent of the necrosis observed in tumor 200 was substantially and unexpectedly greater than would have been expected based upon the teachings of the prior art. This extensive volume of necrosis is believed to have been caused by one or more of the concomitant factors discussed above., The substantially greater volume of necrosis, extending both radially and in depth well beyond the expected fluence zones of the probes, far exceeds that which would have been expected based upon PDT destruction of the abnormal tissue directly illuminated by light from probes 206 and 208 in these zones.

Figure 12:
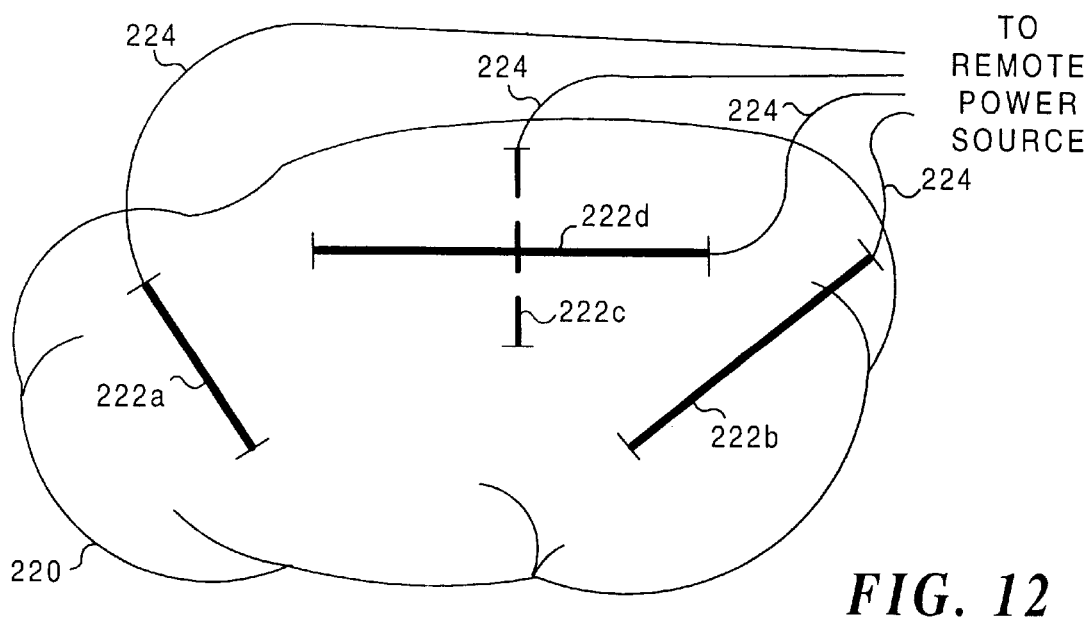
FIG. 12 is a side elevational view of a first pattern of light emitting probes for enhancing the effect of PDT in treating a large volume tumor.
Figure 13:
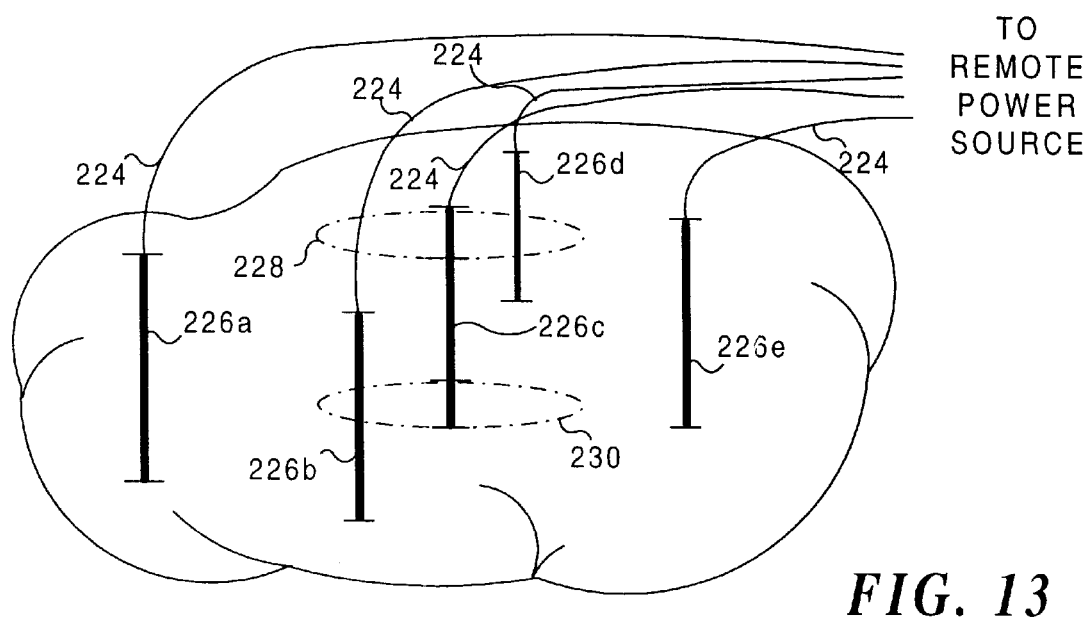
FIG. 13 is a side elevational view of a second pattern of light emitting probes for enhancing the effect of PDT in treating the large volume tumor.

FIGS. 12 and 13 illustrate two further exemplary configurations for placing probes within a tumor 220. In these exemplary configurations, the abnormal tissue comprising the tumor is treated with an appropriate photoreactive agent prior to administration of the extended light therapy. In FIG. 12, probes 222a, 222b, and 222c are angled inwardly so their outwardly extending proximal ends are radially further apart than their inwardly extending distal ends. A probe 222d is inserted generally within the central region of tumor 220, adjacent its upper surface. Leads 224 extend from the probes to a remote power source (not shown) for energizing the probes so that they emit light into the tumor. By positioning probe 222d transversely within the central portion of the tumor, the light pattern provided by the probes should enhance the volume of necrosis resulting from one or more of the concomitant factors discussed above. The interior of tumor 220 should be deprived of oxygen due to the destruction of the vascular system surrounding it and this factor should also enhance the destruction of abnormal tissue resulting from the extended light therapy.

A similar result is achieved using the exemplary configuration of probes 226a–226e within tumor 220 shown in FIG. 13. Again, leads 224 couple these probes to a remote power source (not shown). In this embodiment, each of the probes are generally inserted into tumor 220 so that their longitudinal axes are generally parallel with each other. Probe 226c is inserted into the center of tumor 220 and includes light sources adjacent its proximal and distal ends that are energized to produce a fluence zone 228 and 230 as illustrated in FIG. 13. The volume between fluence zones 228 and 230, which does not receive direct light from any of the probes, is nevertheless destroyed due to the vascular effects caused by destruction of the surrounding abnormal tissue. The oxygen and nutrient supply to the internal portion of tumor 220 is thus cut off due to the necrosis of the vascular system around the periphery of the tumor.

It will be apparent that the probes and leads in the above examples may be replaced with optical fibers coupled to one or more internal or external light sources. In addition, it should be apparent that many other configurations of probes or optical fibers can be employed to achieve the concomitant effects resulting from long-term administration of light therapy in accord with the present invention.

Although the present invention has been described in connection with the preferred forms of practicing it, those of ordinary skill in the art will understand that many other modifications can be made thereto within the scope of the claims that follow. Accordingly, it is not intended that the scope of the invention in any ay be limited by the above description, but instead be determined entirely by reference to the claims that follow.

The invention in which an exclusive right is claimed is defined by the following:

1. A method for destroying abnormal tissue in a tumor within a patient's body using an extended light therapy that directly applies light to less than all of the abnormal tissue in the tumor, comprising the steps of:

(a) providing a plurality of light emitting probes, each light emitting probe being capable of emitting light having a characteristic emission waveband and being adapted to be at least partially inserted into said tumor, light emitted by each light emitting probe generating a fluence zone comprising a volume of tissue surrounding the light emitting probe into which light emitted by the light emitting probe penetrates along a direct path, light emitted by each light emitting probe further inducing at least one concomitant effect that generates a necrotic zone associated with each fluence zone when a corresponding light emitting probe emits light for an extended period of time, each necrotic zone extending substantially beyond the associated fluence zone;

(b) determining a desired treatment zone, said desired treatment zone comprising a portion of said tumor that contains substantially all abnormal tissue that will desirably be destroyed by the extended light therapy and at least one concomitant effect associated with the extended light therapy;

(c) administering a photoreactive agent to the abnormal tissue of the tumor, said photoreactive agent having a characteristic light absorption bandwidth and being preferentially absorbed by the abnormal tissue rather than by normal tissue in the patient's body;

(d) implanting said plurality of light emitting probes in a spaced-apart array within said tumor, said spaced-apart array defining a pattern of the plurality of light emitting probes selected to directly apply light to less than all of the abnormal tissue, and selected such that a union of each necrotic zone associated with an implanted light emitting probe substantially corresponds to said treatment zone;

(e) activating said plurality of light emitting probes to administer light to the abnormal tissue within the fluence zone around each light emitting probe;

(f) continuing to administer the light emitted by the light emitting probes to the abnormal tissue for at least three hours in carrying out the extended light therapy, said light destroying abnormal tissue within each fluence zone by activating the photoreactive agent absorbed thereby; and (g) destroying abnormal tissue that is within the treatment zone but substantially beyond the fluence zone around each light emitting probe, by inducing at least one concomitant effect based upon the extended light therapy, a volume of said treatment zone being substantially greater than a combined volume of the fluence zones around each of the plurality of light emitting probes.

2. A method for destroying abnormal tissue in a tumor within a patient's body using an extended light therapy that directly applies light to less than all of the abnormal tissue in the tumor, comprising the steps of:

(a) providing a plurality of light emitting probes, each light emitting probe being capable of emitting light having a characteristic emission waveband and being adapted to be at least partially inserted into said tumor, light emitted by each light emitting probe generating a fluence zone comprising a volume of tissue surrounding the light emitting probe into which light emitted by the light emitting probe penetrates along a direct path;

(b) administering a photoreactive agent, said photoreactive agent having a characteristic absorption waveband corresponding to the characteristic emission waveband of the plurality of light emitting probes and being preferably absorbed by the abnormal tissue rather than by normal tissue in the patient's body;

(c) implanting said plurality of light emitting probes in a spaced-apart array within said tumor, said spaced-apart array defining a pattern of the plurality of light emitting probes selected to produce at least one concomitant effect that will substantially improve an effectiveness of the extended light therapy, said pattern providing a plurality of non overlapping fluence zones in which light emitted by the plurality of probes is directly applied to less than all of the abnormal tissue in the tumor;

(d) activating said plurality of light emitting probes to administer light to the abnormal tissue within each fluence zone around each light emitting probe;

(e) continuing to administer the light emitted by the light emitting probes to the abnormal tissue for at least three hours in carrying out the extended light therapy, said light destroying abnormal tissue within each fluence zone by activating the photoreactive agent absorbed thereby; and (f) destroying abnormal tissue that is within a desired necrotic zone but substantially beyond the fluence zone around each light emitting probe, by inducing said at least one concomitant effect based upon the pattern in which the plurality of light emitting probes are implanted in the tumor, a volume of the necrotic zone being substantially greater than a combined volume of the fluence zones around each of the plurality of light emitting probes.

3. A method for destroying abnormal tissue in a tumor within a patient's body using an extended light therapy, such that a minor portion of the abnormal tissue destroyed is directly penetrated by light, and a major portion of the abnormal tissue destroyed is not directly penetrated by light, comprising the steps of:

(a) providing a plurality of light emitting probes, each light emitting probe being capable of emitting light having a characteristic emission waveband, being adapted to be at least partially inserted into said tumor, and being capable of generating a fluence zone comprising a region of tissue in said tumor into which light emitted by the light emitting probe penetrates along a direct path;

(b) administering a photoreactive agent, said photoreactive agent being preferentially absorbed by the abnormal tissue rather than by normal tissue in the patient's body and having a characteristic light absorption waveband matching said characteristic emission waveband of the plurality of light emitting probes;

(c) implanting said plurality of light emitting probes into said tumor in a spaced-apart array defining a selected pattern, said pattern being selected such that the minor portion of said abnormal tissue within said tumor is within fluence zones produced around the plurality of light emitting probes, and the major portion of said abnormal tissue is not directly penetrated by light emitted from any of said plurality of light emitting probes, said pattern being further selected to induce a concomitant effect that results in abnormal tissue necrosis beyond an extent of each individual fluence zone;

(d) activating said plurality of light emitting probes;

(e) directing the light from the plurality of light emitting probes in a predefined direction, thereby administering light to a defined portion of the tumor, the defined portion including at least some of the abnormal tissue disposed within the minor portion, to limit administration of the photodynamic therapy to said defined portion of the tumor;

(f) continuing the administration of light to the abnormal tissue in the defined portion of the tumor for an extended treatment period in excess of three hours, said light destroying abnormal tissue within the defined portion of the tumor by activating the photoreactive agent absorbed thereby; and (g) destroying abnormal tissue that is within said major portion of said abnormal tissue, by inducing at least one concomitant effect, thereby destroying the abnormal tissue within said major portion as a result of inducing said at least one concomitant effect.

4. A method for destroying abnormal tissue in a tumor within a patient's body using an extended light therapy that directly applies light to less than all of the abnormal tissue in the tumor, comprising the steps of:

(a) providing a plurality of light emitting probes, each light emitting probe being capable of emitting light having a characteristic emission waveband and being adapted to be at least partially inserted into said tumor, light emitted by each light emitting probe generating a fluence zone comprising a volume of tissue surrounding the light emitting probe into which light emitted by the light emitting probe penetrates along a direct path;

(b) administering a photoreactive agent, said photoreactive agent having a characteristic absorption waveband corresponding to the characteristic emission waveband of the plurality of light emitting probes and being preferably absorbed by the abnormal tissue rather than by normal tissue in the patient's body;

(c) implanting said plurality of light emitting probes in a spaced-apart array within said tumor, said spaced-apart array defining a pattern of the plurality of light emitting probes selected to produce at least one concomitant effect that will substantially improve an effectiveness of the extended light therapy, said pattern providing a plurality of fluence zones in which light emitted by the plurality of probes is directly applied to less than all of the abnormal tissue in the tumor, said pattern comprising a central core section into which there is substantially no direct light penetration;

(d) activating said plurality of light emitting probes to administer light to the abnormal tissue within each fluence zone around each light emitting probe;

(e) continuing to administer the light emitted by the light emitting probes to the abnormal tissue for at least three hours in carrying out the extended light therapy, said light destroying abnormal tissue within each fluence zone by activating the photoreactive agent absorbed thereby; and (f) destroying abnormal tissue that is within a desired necrotic zone but substantially beyond the fluence zone around each light emitting probe, by inducing at least one concomitant effect based upon the pattern in which the plurality of light emitting probes are implanted in the tumor, a volume of the necrotic zone being substantially greater than a combined volume of the fluence zones around each of the plurality of light emitting probes.

5. The method of claim 4, wherein said spaced-apart array comprises a plurality of overlapping fluence zones.

6. The method of claim 4, wherein said spaced-apart array comprises a plurality of non overlapping fluence zones.

7. The method of claim 4, wherein the step of activating said plurality of light emitting probes comprises the step of administering light from at least one light source included on each of the plurality of light emitting probes.

8. The method of claim 4, wherein the step of implanting said plurality of light emitting probes further comprises the step of selecting a pattern that enables abnormal tissue within the desired necrotic zone to be destroyed using as few light emitting probes as possible.

9. The method of claim 8, further comprising the step of selecting said plurality of light emitting probes such that light from each of said plurality of probes penetrates the tumor in the treatment zone to a depth that is not more than about 3 cm.

10. The method of claim 8, wherein the step of activating said plurality of light emitting probes comprises the step of delivering light to the plurality of light emitting probes through a plurality of optical fibers from a source that is external to the patient's body.

11. The method of claim 8, further comprising the steps of:

(a) emitting light into the tumor in a first direction from each of the plurality of probes, said first direction being determine relative to each probe from which the light is emitted and not necessarily identical for each probe;

(b) terminating light emission into the tumor in the first direction; and (c) emitting light into the tumor in a second direction from each of the plurality of probes, said second direction being substantially different from the first direction for each of the probes from which the light is emitted.

12. The method of claim 11, wherein the step of emitting light into the tumor in the first direction comprises the step of emitting light toward a perimeter of the tumor, and the wherein the step of emitting light into the tumor in the second direction comprises the step of emitting light toward an interior of the tumor, light emitted in the first direction causing destruction of the abnormal tissue toward the perimeter of the tumor from each probe, which improves an efficacy with which the light emitted in the second direction destroys the abnormal tissue.

13. A method for destroying abnormal tissue in a tumor within a patient's body using an extended light therapy, such that a minor portion of the abnormal tissue destroyed is directly penetrated by light, and a major portion of the abnormal tissue destroyed is not directly penetrated by light, comprising the steps of:

(a) providing a plurality of light emitting probes, each light emitting probe being capable of selectively emitting light having a characteristic emission waveband in at least one of a first predefined direction and a second predefined direction, each light emitting probe being adapted to be at least partially inserted into said tumor, and each light emitting probe being capable of generating a fluence zone comprising a region of tissue in said tumor into which light emitted by the light emitting probe penetrates along a direct path;

(b) administering a photoreactive agent, said photoreactive agent being preferentially absorbed by the abnormal tissue rather than by normal tissue in the patient's body and having a characteristic light absorption waveband matching said characteristic emission waveband of the plurality of light emitting probes;

(c) implanting said plurality of light emitting probes into said tumor in a spaced-apart array defining a selected pattern, said pattern being selected such that the minor portion of said abnormal tissue within said tumor is within fluence zones produced around the plurality of light emitting probes, and the major portion of said abnormal tissue is not directly penetrated by light emitted from any of said plurality of light emitting probes, said pattern being further selected to induce a concomitant effect that results in abnormal tissue necrosis beyond an extent of each individual fluence zone;

(d) activating said plurality of light emitting probes in an alternating fashion, such that light is only administered in one of the first and the second predefined directions at a time, thereby administering light to the abnormal tissue disposed within the minor portion comprising the fluence zones around each activated light emitting probe;

(e) continuing the administration of light to the abnormal tissue in the minor portion for an extended treatment period in excess of three hours, such that light is administered in both the first and second predefined directions, said light destroying abnormal tissue within the minor portion comprising the fluence zones by activating the photoreactive agent absorbed thereby; and (f) destroying abnormal tissue that is within said major portion of said abnormal tissue, by inducing said at least one concomitant effect, thereby destroying the abnormal tissue within said major portion as a result of inducing said at least one concomitant effect.

14. The method of claim 13, wherein said spaced-apart array comprises a central core section into which there is substantially no direct light penetration.

15. The method of claim 13, wherein said selected pattern comprises a plurality of overlapping fluence zones.

16. The method of claim 13, wherein said selected pattern comprises a plurality of non overlapping fluence zones.

17. The method of claim 13, wherein said selected pattern comprises a central core volume of abnormal tissue that is devoid of any fluence zone.

18. The method of claim 13, wherein the step of administering light to the abnormal tissue comprises the step of producing the light with at least one light source on each of the plurality of light emitting probes.

19. The method of claim 13, wherein the step of administering light to the abnormal tissue comprises the steps of providing a source of light that is external to the patient's body and coupling the source of light to each of the plurality of light emitting probes by a different one of a corresponding plurality of optical fibers.

20. The method of claim 13, wherein the step of providing a plurality of light emitting probes comprises the step of providing a plurality of spaced-apart light sources within each of the plurality of light emitting probes, each spaced-apart light source being capable of selectively emitting light having a characteristic emission waveband in at least one of the first predefined direction and the second predefined direction.

21. The method of claim 13, wherein the plurality of probes are transcutaneously inserted into the tumor.

22. The method of claim 21, further comprising the step of energizing the plurality of probes from an external source of power by transcutaneous transfer of energy.

23. The method of claim 13, further comprising the step of directing the light from the plurality of light emitting probes so as to limit administration of the photodynamic therapy to a defined portion of the tumor.

24. The method of claim 23, wherein the step of providing comprises the step of providing at least one light emitting probe having a reflective surface on one side of the light emitting probe, thereby limiting administration of the light to a direction opposite said reflective surface.

25. A method for destroying abnormal tissue within a tumor in a patient's body using an extended light therapy that directly administers light to only a minor portion of said abnormal tissue, yet results in the destruction of a substantially major portion of said abnormal tissue, comprising the steps of:

(a) administering a photoreactive agent to the abnormal tissue of the tumor, said photoreactive agent having a characteristic light absorption bandwidth and being preferentially absorbed by the abnormal tissue rather than by normal tissue in the patient's body;

(b) disposing a plurality of light probes in a generally circular pattern, each light emitting probe comprising at least a first light source capable of producing a first fluence zone, and at least a second light source capable of producing a second fluence zone, to achieve a desired generally circular spaced-apart pattern of light within the abnormal tissue, such that:

(i) each first and second fluence zone corresponds to a penetration depth of the light into the tumor along a direct path of the light emitted by one of said first and second light sources, said light that is emitted having a waveband corresponding to the absorption waveband of the photoreactive agent, a cumulative total of the first and second fluence zones comprising only a minor portion of said abnormal tissue;

(ii) a necrotic zone in the tumor is defined by each of said first and second fluence zones and by an additional distance beyond the penetration depth of the light into the tumor, such that the necrotic zone encompasses a substantial portion of the tumor not penetrated by the light being administered along the direct path and is thus beyond each first and second fluence zone;

(iii) a portion of a vasculature of said tumor servicing at least a portion of said necrotic zone lies within at least one second fluence zone; and (iv) a periphery of said tumor lies within at least one first fluence zone;

(c) administering the light from said plurality of light emitting probes to the abnormal tissue within each first fluence zone by activating each first light source, thereby directing light toward said periphery but not toward an interior of said tumor, said light activating said photoreactive agent to destroy the abnormal tissue illuminated by the light by providing a photodynamic therapy to each first fluence zone; and (d) continuing the administration of light from said plurality of light emitting probes to the abnormal tissue within each second fluence zone by activating each second light source, thereby directing light toward the interior of said tumor until a secondary effect is produced in the abnormal tissue beyond the first and second fluence zones, said secondary effect causing necrosis of the abnormal tissue outside each first and second fluence zone, but within said necrotic zone, thereby destroying a substantially major portion of the abnormal tissue with the secondary effect, although directly administering light to only a minor portion of said abnormal tissue, said secondary effect comprising at least one of a vascular collapse, a stasis, and an occlusion within said portion of the vasculature.

26. The method of claim 25, wherein said additional distance is no greater than. 5 centimeters, and wherein the step of disposing the plurality of light emitting probes to achieve a desired pattern further comprises the step of positioning the plurality of light emitting probes such that said necrotic zone lies completely within said tumor.

* * * * *